US006998264B2

(12) United States Patent
Ingram

(10) Patent No.: US 6,998,264 B2
(45) Date of Patent: Feb. 14, 2006

(54) REPLICATION OF BIOLOGICAL TISSUE

(75) Inventor: Marylou Ingram, Pasadena, CA (US)

(73) Assignee: Huntington Medical Research Institutes, Pasadena, CA (US)

( * ) Notice: Subject to any disclaimer, the term of this patent is extended or adjusted under 35 U.S.C. 154(b) by 525 days.

(21) Appl. No.: 10/299,245

(22) Filed: Nov. 19, 2002

(65) Prior Publication Data

US 2004/0096966 A1 May 20, 2004

(51) Int. Cl.
*C12N 5/00* (2006.01)
(52) U.S. Cl. ...................... 435/373; 435/325; 435/366; 435/371; 435/383
(58) Field of Classification Search ................ 435/373, 435/371, 325, 366, 383
See application file for complete search history.

(56) References Cited

U.S. PATENT DOCUMENTS

| | | | | | |
|---|---|---|---|---|---|
| 3,893,887 | A | * | 7/1975 | Smith et al. ................. | 435/395 |
| 5,019,495 | A | * | 5/1991 | Shanbrom .................... | 435/1.1 |
| 5,026,650 | A | | 6/1991 | Schwarz et al. | |
| 5,153,131 | A | | 10/1992 | Wolf et al. | |
| 5,282,861 | A | | 2/1994 | Kaplan | |
| 5,308,764 | A | * | 5/1994 | Goodwin et al. ............. | 435/1.1 |
| 5,330,908 | A | | 7/1994 | Spaulding | |
| 5,449,617 | A | * | 9/1995 | Falkenberg et al. ......... | 435/394 |
| 5,496,722 | A | * | 3/1996 | Goodwin et al. ........... | 435/371 |
| 5,523,228 | A | | 6/1996 | Ingram et al. | |
| 5,624,840 | A | | 4/1997 | Naughton et al. | |
| 5,627,021 | A | * | 5/1997 | Goodwin et al. ............. | 435/1.1 |
| 5,863,531 | A | * | 1/1999 | Naughton et al. ......... | 424/93.7 |
| 5,928,936 | A | | 7/1999 | Ingram | |
| 2004/0082063 | A1 | | 4/2004 | Deshpande et al. | |

OTHER PUBLICATIONS

M. Ingram et al., "Invasive Properties of Cells Co-cultured in Simulated Microgravity", Abstract, 1997 Congress on In Vitro Biology, Washington, DC, Jun. 14-18, 1997.

M. Ingram et al., "Three-Dimensional Growth Patterns of Various Human Tumor Cell Lines in Simulated Microgravity of a Nasa Bioreactor", In Vitro Cell. Dev. Biol.—Animal 33:459-466, Jun. 1997, © 1997 Society for In Vitro Biology.
Ingram, "Hepatocyte Histoids for Product Safety Tests", Preproposal to the Johns Hopkins Center for Alternatives to Animal Testing Grants Program 1998-1999, CAAT Abstract Form Jan. 1997 (p. 1), 1997, one page, Huntington Medical Research Institutes, Pasadena, California.
Ingram et al., "Invasive properties of cells co-cultured in simulated microgravity", Abstract submitted for 1997 Congress on in vitro Biology, printed in "Hot Topics" Abstracts In Vitro, 33, (1997), one page, Huntington Medical Research Institutes, Pasadena, California.
Ingram, "Hepatocyte histoids for product testing", Submitted 1998 to the Johns Hopkins Center for Alternatives to Animal Testing in response to successful pre-proposal (1997), Grant Kit Rev. Mar. 1997, 12 pages (p. 2, p. 10 of 20 and pp. 11-20.).
Ingram et al., "Three-Dimensional Growth Patterns of Various Human Tumor Cell Lines in Simulated Microgravity of a NASA Bioreactor", In Vitro Cell. Dev. Biol.-Animal, Jun. 1997, vol. 33, pp. 459-466, Society for In Vitro Biology.
Cell Control Sciences, LLC, "Control your Immuno", Spring 2001, pp. 1-4, Richmond, Virginia.

* cited by examiner

*Primary Examiner*—Leon B. Lankford, Jr.
(74) *Attorney, Agent, or Firm*—Christie, Parker & Hale, LLP

(57) ABSTRACT

Biological tissues are grown in a low shear, microgravity environment by culturing connective tissue cells to form a three-dimensional structure, which is thereafter co-cultured with endothelial and epithelial cells to replicate naturally occurring tissues. Preferably, the three-dimensional connective tissue cells are first cultured with endothelial cells to form three-dimensional structures of connective tissue cells and endothelial cells, which are thereafter co-cultured with epithelial cells to replicate naturally occurring tissue. The cultured tissue is in the general shape of spheroids having a diameter between about 0.1 mm and about 5 m.

16 Claims, No Drawings

REPLICATION OF BIOLOGICAL TISSUE

FIELD OF THE INVENTION

This invention relates to cultured biological tissue which replicates naturally occurring tissue.

BACKGROUND OF THE INVENTION

For many years, workers in the art and science of cell and tissue culture have recognized the importance of growing cells and tissues under conditions that produce results which replicate cells and tissues occurring naturally in animals.

Cultured cells and tissues can be produced in unlimited quantities, and, if they closely imitate the natural product, can be used in many important ways. For example, cultured cells and tissues can be used as reference standards by surgical pathologists when processing specimens of patients' tissue taken for diagnosis of various diseases.

Surgical pathologists are presented daily with puzzles in the form of tissue specimens removed during surgery or various biopsy procedures. The experienced pathologist makes a diagnosis based on the microscopic structure (morphology) of the tissue and multiple clues about its composition. Those clues include specific molecules produced in the tissue through the action of one or more genes, including mutant genes, and they are identified by employing special staining methods to make them visible through a microscope. Those molecules are commonly referred to as "markers".

When a patient's tissue specimen is submitted to a pathologist, it is first "fixed" by exposing it to a preservative solution, such as formalin. The fixed tissue is then embedded in a small block of paraffin, and the block is sliced with a microtome into thin slices or "sections", typically four to eight microns thick. Individual sections are attached to standard glass microscope slides, processed to remove the paraffin, and thereafter stained using any of a variety of staining methods known to pathologists. For example, immunostaining is a type of staining in which the tissue section is exposed to a highly specific antibody which binds only to a specific marker in the tissue. The tissue is then treated to produce a colored reaction product at the site of antibody deposition so the presence, location and relative amount of marker in the tissue can be observed by conventional or automated microscopy. However, variations in any step in tissue processing, or staining, or in the chemicals used produce variations in the final staining.

Identification of specific markers is important in the diagnosis and classification of tumors, but without dependable reference standards, interpretation of immunostained specimens is arbitrary and non-quantitative. Variation in results within the same laboratory, to say nothing of variation among different laboratories, limits the utility of this potentially powerful technology. It would be relatively easy to adjust for operational variables, if reliable standard reference tissues were available. However, no single specimen of any naturally occurring tissue is large enough to provide specimens for numerous laboratories repeatedly over long periods. For example, about 30 million paraffin-embedded tissue blocks are prepared each year in the United States alone, and 10–15% of them require immunostaining.

A paper entitled "Three-Dimensional Growth Patterns of Various Human Tumor Cell Lines in Simulated Microgravity of a NASA Bioreactor" by M. Ingram, et al., in *In Vitro Cell. Dev. Biol.-Animal* 33:459466, June 1997, describes preliminary experiments in which human tumor cells were co-cultured with fibroblast cells. Although those experiments were encouraging, they did not produce tissues which closely replicate natural tissue.

SUMMARY OF THE INVENTION

This invention provides improved methods for growing unique biological tissues which closely resemble natural tissues, and therefore can be used as reliable standard reference tissues, as well as for other important purposes. The tissues grown in accordance with this invention have a three-dimensional structure which closely replicates naturally occurring tissue. These three-dimensional tissue-like structures, or constructs, are referred to herein as "histoids". They are generated spontaneously during co-culture, under special conditions, of the major cell types to be included in the tissue. To produce a tumor histoid, for example, cell lines representing each major cell type of the tumor are selected so that at least one of the types expresses one or more markers of interest. The selected cells are co-cultured in a bioreactor chamber similar to that described in U.S. Pat. No. 5,523,228 to Ingram, et al., or U.S. Pat. No. 5,928,936 to Ingram. The disclosure of each of these two patents is incorporated herein by reference. The co-culturing promotes cell interaction that results in histoids, typically generally spheroidal bodies from about 0.1 mm to about 5 millimeters in diameter. When fixed, sectioned and stained, the histoids look so much like actual tumor tissue they are almost indistinguishable when examined by microscopy. Using appropriate methods, the histoids made in accordance with this invention can be shipped unfixed so that they may be included as a "standard" with a tissue specimen of a patient's tumor during all stages of tissue processing and staining. Thus, the standard tissue and the patient's tissue are subjected to identical processing conditions, resulting in a more reliable diagnosis.

The histoids of this invention are not limited to serving as standards in tissue processing and staining. They can also serve as realistic and reliable tumor models in screening anti-cancer pharmaceuticals or gene therapies. Histoids which replicate normal human tissue can also be used in tissue engineering, such as in liver assist devices, pancreas assist systems, and as "seeds" in tissue repair protocols, as well as in growing artificial organs.

In a preferred method of the invention, a suspension of connective tissue cells is cultured under low shear stress in a nutrient in a rotatable bioreactor chamber for one to four days to generate spheroids of connective tissue cells. The chamber includes a flexible wall which is permeable to gas, but impermeable to liquid. Fibroblast, myofibroblast, bone, and cartilage cells are examples of connective tissue cells useful in this invention. Fibroblast or myofibroblast cells are presently preferred. Preferably, the bioreactor chamber is rotated around a horizontal axis at about 12 rpm in a fully humidified tissue culture incubator at 37° C. while surrounded by an atmosphere of air and about 5% carbon dioxide, by volume.

After connective tissue spheroids of desired size are formed, the rotation of the bioreactor chamber is stopped, and the chamber is removed from the incubator. Some of the nutrient is removed from the bioreactor chamber and replaced with an equal volume of endothelial cell growth medium, along with endothelial cells, which are preferably of the microvascular cell type. Thereafter, the rotatable bioreactor chamber is placed in an incubator which has an atmosphere of about 5% oxygen and about 95% nitrogen, by volume. The incubator temperature is kept at about 37° C., and relative humidity is about 100%. The bioreactor chamber is rotated at about 12 rpm for about 24 hours. Used nutrient is removed from the bioreactor chamber, and replaced with fresh endothelial growth medium, and rotation in the humidifier is continued for another 24 hours. Thereafter, rotation of the bioreactor chamber is stopped, and epithelial cells, such as breast cancer cells, are added to the bioreactor chamber with a suitable nutrient. The bioreactor chamber is returned to the incubator and rotated at about 12 rpm in an atmosphere of 5% carbon dioxide and air at 37° C. and about 100% humidity. Culturing is continued for about seven days, interrupting once every 24 hours to remove some spent nutrient solution and replace it with fresh nutrient solution. At the end of the culture period, the cells have produced small spheroidal histoids that contain a central zone of connective tissue cells which have been invaded by endothelial cells that produce rudimentary, capillary-like channels. The breast cancer epithelial cells have coated the surface of the histoid with an epithelium-like layer, and have invaded the core of connective tissue cells. These histoids are harvested from the bioreactor, and are ready for routine fixation. Standard histological procedures are followed thereafter to section and stain the histoids. Alternatively, tumor histoids are used to screen pharmaceuticals. Non-tumor histoids, i.e., those made with non-malignant epithelial cells, can also be used for screening pharmaceutical aid for tissue engineering.

DETAILED DESCRIPTION OF THE INVENTION

For each type of biological tissue or cell grown in accordance with this invention, culture details must be customized in terms of cell lines selected, optimum number of cells of each type introduced into a bioreactor culture chamber, sequence of adding cells, duration of culture after addition of each cell type, gaseous composition of atmosphere in a tissue culture incubator surrounding the bioreactor chamber, composition of nutrient medium, and amount and type of additives, such as growth factors and cytokines. The following example describes in detail a presently preferred method for generating breast cancer histoids in accordance with this invention.

The method uses a bioreactor culture chamber similar to that described in U.S. Pat. No. 5,523,228 or U.S. Pat. No. 5,928,936.

In this example, there are three major stages in histoid production. Each stage introduces a preferred cell type into the bioreactor culture chamber. The various cell lines used are first grown in conventional monolayer cultures. Cells harvested from the monolayer cultures are introduced into the bioreactor chamber as a monodisperse suspension, i.e., a dispersion of single cells, and rotation of the bioreactor chamber begins promptly to maintain the cells in suspension. All steps of the procedure are carried out using rigorous aseptic techniques.

For the following example, human breast cancer cells expressing HER-2neu are obtained as an established cell line, SKBR 3, from American Type Culture Collection (ATCC) in Manassas, Va. These cells are established as a monolayer flask culture in a conventional tissue culture flask, and maintained as a proliferating population to provide cells for histoid production. The other two cell lines, namely, fibroblast cells (WI38) and human microvascular endothelial cells (HMVEC) are purchased from ATCC, and from Clonetics, Inc., respectively. These two cell lines are also established and maintained as monolayer flask cultures using conventional tissue culture methodology. Detailed composition of the various solutions used in the process is set forth in the table following the detailed description.

Stage 1. Generating Spheroids of Fibroblast Cells (WI38) (Connective Tissue Cells):

a. Select a tissue culture flask that contains a near-confluent monolayer of WI38 fibroblast cells, and aspirate the liquid medium (DMEMF12) overlying the cell layer into a pipette, and discard the liquid.

b. Wash (flood) the layer of fibroblast cells in the culture flask with EDTA/HBS solution, which binds and removes calcium and magnesium ions from the remaining medium.

c. Aspirate the wash solution of step b. into a pipette, and discard the wash solution.

d. Repeat steps b. and c.

e. Add one ml. of trypsin solution to flood the fibroblast cells, and allow the solution to stand in contact with the cells for a few minutes until the cells are freed from their attachment to the flask surface and float free. (Trypsin is an enzyme which digests proteinaceous material which attaches the cells to the flask surface.)

f. Add one drop (about 0.05 to about 0.5 ml.) of DNAse solution (contains an enzyme which dissolves free DNA associated with the cells). Then add 9 ml. of DMEMF12 nutrient medium which contains 10% fetal bovine serum by volume to stop the action of the trypsin.

g. Using a pipette, transfer cells (which are now in suspension) to a centrifuge tube. Flood the culture flask with 10 ml. of DMEMF12 medium, and transfer the "wash" (with any residual cells) to the centrifuge tube.

h. Aspirate the cell suspension in the centrifuge tube into a pipette, and discharge the suspension into the same tube. Repeat several times to break up clumps and produce a uniformly dispersed cell suspension.

i. Determine the cell number by counting cells in the cell suspension using a conventional hemocytometer.

j. Transfer a volume of cell suspension containing five million cells to a 15 ml. centrifuge tube, and centrifuge at 200 times gravity for 10 minutes to produce a cell pellet.

k. Aspirate supernatant liquid from the centrifuge tube, and discard the liquid.

l. Resuspend the cells in the pellet in the centrifuge tube in 10 ml. of DMEMF12 nutrient medium that contains 10% fetal bovine serum by volume, and aspirate the cell suspension into a 10 ml. hypodermic syringe via a 14 gauge cannula.

m. Replace the 14 gauge cannula with a 25 gauge hypodermic needle, and inject the cell suspension into a 10 ml. circular bioreactor culture chamber (of a type similar to that disclosed in U.S. Pat. No. 5,523,228 or U.S. Pat. No. 5,928,936) through the injection port in the chamber. The culture chamber should be completely filled with liquid (no bubbles). As disclosed in U.S. Pat. No. 5,928,936, the bioreactor chamber has flexible walls made of a material (say, silicone or teflon) which is permeable to oxygen and carbon dioxide gas, and impermeable to liquid. The chamber includes a hypodermic syringe injection port to permit access by injection with a needle or cannula.

n. Mount the filled bioreactor chamber to be rotatable about a horizontal axis (as disclosed in U.S. Pat. No. 5,523,228) in a conventional tissue culture incubator, which contains an atmosphere of air with 5% carbon dioxide by volume, and which keeps the temperature of the ambient atmosphere humidified to about 100% relative humidity and at 37° C. Rotate the bioreactor chamber at about 12 rpm.

o. Rotate the bioreactor chamber for 24 hours, during which the fibroblast cells produce multiple small spheroids, which are between about 0.1 mm. and about 1 mm. in diameter, some of which may fuse to form larger bodies.

Stage 2. Addition of Endothelial Cells to the Spheroids of Fibroblast Cells:

a. Remove the bioreactor chamber from the humidifier, and transfer it to a conventional tissue culture hood, keeping the injection port of the bioreactor chamber in the uppermost position.

b. Allow the bioreactor chamber to stand for several minutes until the spheroids of fibroblast cells settle out.

c. Using a syringe fitted with a 25 gauge hypodermic needle, puncture the rubber cap on the injection port, and carefully aspirate to remove about 5 ml. of liquid medium, without disturbing the spheroids of fibroblast cells.

d. Using a separate syringe and needle, add 5 ml. of human microvascular endothelial cell culture (HMVEC-C) growth medium to the bioreactor chamber, and let stand while the spheroids of fibroblast cells settle out. The HMVEC-C growth medium is obtained from Clonetics, Inc. in San Diego, Calif. Alternatively, use human umbilical vein endothelial cell culture (HUVEC-C) growth medium, which has the following composition:

DMEM/F12 Basal Medium
Fetal Bovine Serum, 10–15%, v/v
Heparin, 100 $\mu$g,ml
Endothelial Growth Cell Supplement (ECGS)[1], 30 $\mu$g/ml
Penicillin, 100 units/ml
Streptomycin, 100 $\mu$g/ml
Amphotericin B, 0.25 $\mu$g/ml e. Select a tissue culture flask that contains a near-confluent layer of human microvascular endothelial cells (HMVEC) which have been cultured in endothelial cell medium, and repeat steps a. through j. described above in Stage 1, but substitute endothelial growth medium for DMEMF12.

[1] Purchased from Sigma-Aldrich Fine Chemicals, Inc. in St. Lois, Mo.

f. Resuspend the five million (centrifuged) human microvascular endothelial cells (HMVEC) (see Stage 1, step j.) in 5 ml. of endothelial cell growth medium.

g. The spheroids of fibroblast cells from the Stage 1 culture will have settled out in the bioreactor culture chamber so that most of the supernatant medium can be aspirated into a separate syringe fitted with a 25 gauge needle, and without disturbing the spheroids. To avoid collapsing the flexible walls of the bioreactor chamber and possibly damaging the fibroblast spheroids, insert a second 25 gauge hypodermic needle into the rubber cap on the injection port to serve as a vent during the aspiration, which removes as much supernatant liquid as possible without removing cell particulates.

h. After most of the supernatant liquid is aspirated from the bioreactor chamber, use a syringe fitted with a 14 gauge cannula to aspirate the five million human microvascular endothelial cells (HMVEC) from step f. in Stage 2.

i. Replace the 14 gauge cannula with a 25 gauge hypodermic needle, and inject the suspension of five million endothelial cells into the bioreactor chamber that contains the spheroids of fibroblast cells.

j. Using a separate syringe and needle, inject sufficient additional endothelial cell growth medium (HMVEC-C or HUVEC-C) to fill the culture chamber. This requires less than 5 ml. because the fibroblast cells and some residual medium occupy part of the chamber volume. Remove the second 25 gauge venting needle referred to in step g. of Stage 2.

k. Mount the filled bioreactor chamber to be rotatable about a horizontal axis in a conventional incubator which has an atmosphere of 5% oxygen, 5% $CO_2$, and 90% nitrogen. The incubator maintains a temperature of 37° C. and a relative humidity of about 100%. Rotate the bioreactor chamber in the incubator at 12 rpm.

l. Maintain rotation of the bioreactor in the incubator for 24 hours.

m. After 24 hours of rotation, remove the bioreactor chamber from the incubator, and transfer the chamber to a tissue culture hood while maintaining the injection port of the chamber in the most upright position.

n. Allow particulates to settle in the bioreactor chamber.

o. Using a syringe fitted with a 25 gauge needle, aspirate about 5 ml. of supernatant medium and discard.

p. Using a syringe fitted with a 25 gauge needle, add 5 ml. of endothelial growth medium. Then transfer the bioreactor chamber back into an incubator that has an atmosphere of 5% oxygen, 5% $CO_2$, and 90% nitrogen. While maintaining a temperature of 37° C. and relative humidity of about 100% in the incubator, resume rotating the bioreactor chamber at about 12 rpm for another 24 hours. During this culturing stage, the human microvascular endothelial cells (HMVEC) invade the spheroids of connective tissue to form rudimentary, capillary-like channels. This is confirmed by immunostaining some selected spheroids with an antibody against the patelet-endothelial cell adhesion molecule (PECAM-1), a marker designated as CD31, and which is an excellent identifier of HMVEC.

Stage 3. Addition of Malignant Breast Cells (Epithelial Cells):

a. Remove bioreactor chamber from the incubator, and transfer it to a tissue culture hood, maintaining the chamber with the port in the most upright position as before so particulates settle out away from the port.

b. Select a tissue culture flask which contains a near-confluent layer of breast cancer cells (epithelial cells SKBR3) and, using a pipette, aspirate and discard the medium overlying the layer of epithelial cells.

c. Wash the culture flask surface and cells with EDTA/HBS as described above for the other two flasks.

d. Aspirate and discard the wash liquid.

e. Repeat wash, and discard second wash.

f. Add 1 ml. of trypsin solution to flood the surface of the epithelial cells in the flask and allow to stand until the cells are freed from attachment to the flask.

g. Add one drop (between about 0.5 and 0.05 ml.) of DNAse solution, then 9 ml. of DMEMF12 medium that contains 10% fetal bovine serum by volume.

h. Transfer the epithelial cells that are now in suspension to a centrifuge tube. Flood the culture flask (which held the epithelial cells) with 10 ml. of DMEMF12 medium (with 10% fetal bovine serum by volume), and transfer the "wash" to the same centrifuge tube which holds the suspension of epithelial cells.

i. Aspirate the suspension of epithelial cells in the centrifuge tube into a pipette, and discharge the suspension into the same centrifuge tube. Repeat several times to break up clumps and obtain a uniform suspension of epithelial cells.

j. Determine cell number by counting epithelial cells using a hemocytometer.

k. Transfer a volume of suspension that contains 2.5 million epithelial cells to a 15 ml. centrifuge tube, and centrifuge at 200 times gravity for 10 minutes to produce a pellet of epithelial cells.

l. Aspirate the supernatant liquid from the centrifuge tube, and discard the liquid.

m. Resuspend the epithelial cells in the pellet in 5 ml. of DMEMF12 nutrient medium that contains 10% fetal bovine serum by volume and 20 nanograms of vascular endothelial growth factor (VEGF), available from Sigma-Aldrich Fine Chemicals, Inc. in St. Lois, Mo.

n. Using a 10 ml. syringe fitted with a 14 gauge cannula, aspirate the suspension of epithelial cells from the centrifuge tube.

o. Replace the 14 gauge cannula with a 25 gauge hypodermic needle.

p. Using a separate syringe fitted with a 25 gauge needle, aspirate and discard 5 ml. of supernatant medium from the upright bioreactor chamber.

q. Inject the suspension of epithelial cells in the syringe into the bioreactor chamber.

r. Return the bioreactor chamber to the incubator, which has an atmosphere of 5% carbon dioxide and air at 37° C., and a relative humidity of about 100%. Resume rotating the bioreactor chamber about a horizontal axis at about 12 rpm.

s. Continue culturing the three types of cells in the bioreactor chamber for seven days, interrupting once every 24 hours to remove 5 ml. of used nutrient medium and add 5 ml. of fresh nutrient medium of the same composition as in Stage 3, step m. This is accomplished by aspirating and discarding 5 ml. of supernatant used nutrient medium from the bioreactor chamber (after first allowing particulates to settle out), using a 10 ml. hypodermic syringe fitted with a 25 gauge needle, and injecting fresh nutrient medium using a second syringe fitted with a 25 gauge needle. The bioreactor chamber is then returned to the incubator with the atmosphere of 5% carbon dioxide and air at 37° C. and about 100% humidity. Rotation is resumed for another 24 hours.

t. At the end of the culture period, the cells produce multiple small histoids that are generally spheroidal in shape, and contain a central zone or inner core of fibroblast cells which has been invaded by endothelial cells to produce rudimentary, capillary-like channels. The histoids are between about 0.1 mm and about 5 mm in diameter. The breast cancer epithelial cells coat the periphery of the histoids with an epithelium-like layer, which also extends into the fibroblast central zone, just as naturally occurring malignant cells invade supporting tissue in a patient. These histoids are harvested by aspirating the contents of the bioreactor chamber via the injection port using a large gauge (16–18 gauge) needle on a syringe, or by removing the rubber cap in the injection port, and pouring out the contents. The contents of the bioreactor are collected in a 15 ml. centrifuge tube and centrifuged at 200 times gravity for five minutes. The supernatant liquid is removed and discarded leaving a pellet of histoids, which are resuspended in Hank's Balanced Salt Solution to wash the histoids, which are re-centrifuged. The supernatant liquid is removed and discarded, and the histoids are resuspended in a standard 10% formalin solution buffered to a pH 7 for 24 hours at room temperature for routine fixation. For example, the fixing solution is removed and replaced with 70% alcohol for 24 hours, after which the histoids are processed by routine paraffin embedding. Standard histological procedures are followed thereafter to section and stain the histoids, which closely resemble naturally occurring breast cancer tissue.

Table of Solutions Used in Foregoing Process

DMEMF12: 1:1 (by volume) mixture of Dulbecco's Modified Eagle's Medium and Ham's F12 Medium. The mixture has the following composition:

| COMPONENT (Grams/Liter) | DMEM/F12 (g/L) |
|---|---|
| INORGANIC SALTS | |
| Ammonium Molybdate-4H20 | — |
| Ammonium Metavanadate | — |
| Calcium Chloride | — |
| Calcium Chloride.2H2O | 0.1545 |
| Cobalt Chloride-6H2O | — |
| Cupric Sulfate-5H2O | 0.0000013 |
| Ferric Nitrate-9H20 | 0.00005 |
| Ferrous Sulfate-7H20 | 0.000417 |
| Magnesium Choride (anhydrous) | |
| Magnesium Chloride-6H20 | 0.0612 |
| Magnesium Sulfate (anhydrous) | 0.04884 |
| Manganese Chloride-4H20 | — |
| Manganese Sulfate | — |
| Manganese Sulfate-H20 | |
| Nickel Chloride-6H20 | — |
| Potassium Chloride | 0.3118 |
| Potassium Phosphate Monobasic (Anhydrous) | — |
| Sodium Acetate (anhydrous) | — |
| Sodium Bicarbonate | 1.2 |
| Sodium Chloride | 6.996 |
| Sodium Metasilicate-9H20 | — |
| Sodium Phosphate Dibasic (anhydrous) | 0.07102 |
| Sodium Phosphate Monobasic (anhydrous) | 0.0543 |
| Sodium Selenite | — |
| Stannous Chloride | — |
| Zinc Sulfate-7H20 | 0.000432 |
| AMINO ACIDS | |
| L-Alanine | 0.00445 |
| L-Arginine (free base) | — |
| L-Arginine-HCI | 0.1475 |
| L-Asparagine-H20 | 0.0075 |
| L-Aspartic Acid | 0.00665 |
| L-Cysteine (free acid) | — |
| L-Cysteine-HCI-H20 | — |
| L-Cysteine-2HCI | 0.03129 |
| L-Cystine | — |
| L-Cystine-2HCI | — |
| L-Cystine-2HCI-H20 | 0.01756 |
| L-Glutamic Acid | 0.00735 |
| L-Glutamine | 0.365 |
| Glycine | 0.01875 |
| L-Histidine (free base) | — |
| L-Histidine-HCI-H20 | 0.03148 |
| L-Isoleucine | 0.0545 |
| L-Leucine | 0.059 |
| L-Lysine-HCI | 0.09125 |
| L-Methionine | 0.017 |
| L-Phenylalanine | 0.03548 |
| L-Proline | 0.01725 |
| L-Serine | 0.02625 |
| L-Threonine | 0.05345 |
| L-Tryptophan | 0.00902 |
| L-Tyrosine-Na | — |
| L-Tyrosine-2Na-2H20 | 0.05579 |
| L-Valine | 0.05285 |
| VITAMINS | |
| Ascorbic Acid-Na | — |
| Ascorbic Acid | — |
| D-Biotin | 0.0000035 |
| Calciferol | — |
| Choline Choride | 0.00898 |
| Folic Acid | 0.00266 |
| Folinic Acid (Calcium) | |
| Inositol | — |
| myo-Inositol | 0.0126 |
| Menadione (Vitamin K) | — |

-continued

| COMPONENT (Grams/Liter) | DMEM/F12 (g/L) |
|---|---|
| Niacinamide | 0.00202 |
| D-Pantothenic Acid (hemicalcium) | 0.00224 |
| Pyridoxal-HCl | 0.002 |
| Pyridoxine-HCl | 0.000031 |
| Retinol Acetate | — |
| Riboflavin | 0.000219 |
| Thiamine-HCl | 0.00217 |
| D-alpha-Tocopherol Phosphate-Na | — |
| Vitamin B-12 | 0.00068 |
| Other | |
| Adenine-HCl | — |
| D-Glucose | 3.15 |
| Glutathione (reduced) | — |
| HEPES | 3.5745 |
| Hypoxanthine | 0.0021 |
| Hypoxanthine-Na | |
| Linoleic Acid | 0.000042 |
| Methyl Linoleate | — |
| Phenol Red-Na | 0.00863 |
| Putrescine-2HCl | 0.000081 |
| Pyruvic Acid-Na | 0.055 |
| Thioctic Acid | 0.000105 |
| Thymidine | 0.000365 |
| SPECIFICATION | |
| Osmolality with Na bicarbonate | 299 |

HBSS: Hank's balanced salt solution (g/L: 0.4 KCl, 0.06 potassium phosphate monobasic (anhydrous), 0.35 NaHC0$_3$, 8.0 NaCl, 0.04788 sodium phosphate dibasic (anhydrous), 1.0 0-glucose, and 0.011 phenol red-Na). The pH of the solution is between 7.0 and 7.6.

EDTA/HBS: One milli molar (mM) (ethylenedinitrilo)-tetraacetic acid prepared in HBSS.

Trypsin Solution: 0.05% trypsin, 0.53mM EDTA in HBSS, or 1% trypsin by weight in HBSS.

DNAse Solution: 3mg/ml deoxyribonuclease I in culture medium.

Fetal Bovine Serum: Serum taken from fetus of a cow.

Endothelial Cell Growth Medium.

The above procedure can also be used to produce other types of histoids with malignant tumors, such as prostate cancer, pancreatic cancer, lung cancer, and any of the many other types of epithelial cancer. For example, other cell lines can be selected to express estrogen receptor (ER) or progesterone receptor (PR). Myofibroblast, bone or cartilage cells can be used in place of, or with, the fibroblast cells described in the preceding example.

A pulsing environment is used for the contents of the bioreactor chamber to simulate more closely the pulsing conditions experienced by cells growing in the human body. This is achieved by using a fixed cam adjacent the rotating bioreactor chamber to engage external protuberances (not shown in U.S. Pat. No. 5,523,220 or 5,928,936) on the flexible wall of the chamber. For example, 3 to 5 protuberances induce a pulsing rate between 36 and 60 times per minute, when the chamber rotates at 12 rpm.

Alternatively, the bioreactor chamber is pulsed by gently and periodically engaging it with a roller (not shown in U.S. Pat. No. 5,523,220 or 5,928,936) mounted on the end of a shaft adapted to be driven by an electrical solenoid, which is pulsed at an appropriate rate, say 30 to 70 times per minute, by application of an electrical current intermittently to the solenoid.

The pulsing increases and decreases the pressure in the liquid in bioreactor chamber to simulate that which occurs in humans. For example, the pressure in the chamber is varied from a minimum of about 30 mm Hg to a maximum of about 180 mm Hg above atmospheric pressure at a pulse rate between about 30 and about 80 times per minute or lightly fixed (say, by freezing or treatment with a dilute solution of sodium azide).

Using appropriate methods, the histoids prepared in accordance with this invention can be shipped unfixed so they can be included with a specimen of a patient's tumor during all stages of tissue processing and staining. This procedure helps cancel out variability in staining attributable to steps in tissue processing, other than the staining step itself. Alternatively, as indicated above, the histoids with tumors prepared in accordance with this invention can be fixed before shipment for use as stand-alone standards for staining methods and reagents.

Although the specific example given above explains how to create histoids which contain tumors, histoids or tissues other than tumors are grown in the same way for tissue engineering applications, e.g., in liver assist devices, pancreas assist systems, and as "seeds" in tissue repair protocols, by using non-malignant, normal cells.

I claim:

1. A method for replicating biological tissue, the method including the steps of:
    a) culturing connective tissue cells in a nutrient medium in a bioreactor chamber to produce spheroids of connective tissue cells; thereafter
    b) adding endothelial cells to the bioreactor chamber to contact the spheroids of the connective tissue cells in the presence of a nutrient medium and cause the endothelial cells to invade the spheroids of connective tissue cells; and thereafter
    c) adding epithelial cells to the bioreactor chamber to contact the spheroids of connective tissue cells invaded with endothelial cells in the presence of a nutrient medium and cause the epithelial cells to form a tissue-like layer on the spheroids.

2. A method according to claim 1 in which the bioreactor chamber is rotated about a substantially horizontal axis to provide low shear stress during culturing of the cells.

3. A method according to claim 2 in which the bioreactor chamber includes a wall permeable to gas and impermeable to liquid, and in which the bioreactor chamber is rotated in an atmosphere which includes carbon dioxide in an amount substantially greater than that in the earth's atmosphere.

4. A method according to claim 3, in which the bioreactor chamber is rotated in an atmosphere of air and about 5% carbon dioxide by volume.

5. A method according to claim 3 in which the chamber is isolated in an atmosphere which contains substantially less than about 20% oxygen by volume during the culturing of the endothelial cells.

6. A method according to claim 3 in which the chamber is rotated in an atmosphere of about 5% oxygen and about 95% nitrogen by volume during the culturing of the endothelial cells.

7. A method according to claim 3 in which the bioreactor chamber is rotated in an atmosphere of about 5% carbon dioxide in air by volume during the culturing of the connective tissue cells and during the culturing of the epithelial cells.

8. A method according to claim 3, in which the bioreactor chamber is rotated in an atmosphere of about 5% carbon dioxide in air by volume during the culturing of the connective tissue cells and during the culturing of the epithelial cells, and is rotated in an atmosphere of about 5% oxygen and about 95% nitrogen by volume during the culturing of the endothelial cells.

9. A method according to claim 3 in which the replicated biological tissue is made by using malignant epithelial cells, and is processed and stained simultaneously with a tissue specimen from a patient suspected of having a tumor of the same, type as that of the epithelial cells.

10. A method according to claim 3 in which the cells are subjected to periodic change in pressure during the culturing process.

11. A method according to claim 10 in which the process changes at a rate between about 30 and about 80 times per minute, and the pressure in the chamber varies from a minimum of about 30 mm Hg to a maximum of about 180 mm Hg above atmospheric pressure.

12. A method according to claim 3 in which the number of connective tissue cells is substantially greater than that of the number of epithelial cells.

13. A method according to claim 3 in which the number of connective tissue cells is about twice that of the number of epithelial cells.

14. A method according to claim 3 in which the number of connective tissue cells and the number of endothelial cells are each substantially greater than the number of epithelial cells.

15. A method according to claim 3 in which the number of connective tissue cells and the number of endothelial cells are each about twice that of the number of epithelial cells.

16. A method according to claim 3 in which the endothelial cells are of the microvascular type.

* * * * *